United States Patent
Smith et al.

(10) Patent No.: US 10,682,166 B2
(45) Date of Patent: *Jun. 16, 2020

(54) METHODS AND INSTRUMENTS FOR PERFORMING LEVERAGED REDUCTION DURING SINGLE POSITION SPINE SURGERY

(71) Applicant: NuVasive, Inc., San Diego, CA (US)

(72) Inventors: Tyler G. Smith, Gold River, CA (US); Michael Krasovic, San Diego, CA (US); Brian Wade Adams, Rocklin, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,655

(22) Filed: May 21, 2018

(65) Prior Publication Data

US 2018/0333175 A1 Nov. 22, 2018

Related U.S. Application Data

(63) Continuation of application No. 15/158,925, filed on May 19, 2016, now Pat. No. 9,974,577.

(60) Provisional application No. 62/165,078, filed on May 21, 2015.

(51) Int. Cl.
*A61B 17/88* (2006.01)
*A61B 17/70* (2006.01)

(52) U.S. Cl.
CPC .......... *A61B 17/7076* (2013.01); *A61B 17/70* (2013.01); *A61B 17/7083* (2013.01); *A61B 17/708* (2013.01)

(58) Field of Classification Search
CPC . A61B 17/7076; A61B 17/70; A61B 17/7083; A61B 17/708
USPC ....... 606/246, 279, 90, 96, 97, 99, 102, 104, 606/105, 86 A
See application file for complete search history.

(56) References Cited

U.S. PATENT DOCUMENTS

| | | | |
|---|---|---|---|
| 4,282,217 A | 8/1981 | Baglioni |
| 4,316,169 A | 2/1982 | Teranishi |
| 4,450,899 A | 5/1984 | Jakobsson |
| 5,217,497 A | 6/1993 | Mehdian |
| 5,360,431 A | 11/1994 | Puno |
| 5,474,555 A | 12/1995 | Puno |

(Continued)

FOREIGN PATENT DOCUMENTS

| | | |
|---|---|---|
| DE | 202012102895 U1 | 8/2012 |
| EP | 1891904 A1 | 2/2008 |

(Continued)

*Primary Examiner* — Pedro Philogene
*Assistant Examiner* — David C Comstock (57) ABSTRACT

A spinal procedure includes attaching a first reduction instrument to a first guide assembly and a second guide assembly. The first reduction instrument includes a fixed attachment assembly and a translating attachment assembly that cooperatively interfaces the fixed attachment assembly. The first guide assembly is attached to a first pedicle and the second guide assembly is attached to a second pedicle. The first reduction instrument is moved to reduce an orientation of the spine, while imaging a reduction of the orientation of the spine. An angle and position of the first reduction instrument is locked upon achieving a desired reduction. The spine may then be fused.

15 Claims, 7 Drawing Sheets

(56) References Cited

U.S. PATENT DOCUMENTS

| | | |
|---|---|---|
| 5,496,321 A | 3/1996 | Puno |
| 5,651,319 A | 10/1997 | Biedermann |
| 5,716,356 A | 2/1998 | Biedermann |
| 5,910,141 A | 6/1999 | Morrison |
| 5,941,885 A | 8/1999 | Jackson |
| 6,059,786 A | 5/2000 | Jackson |
| 6,139,549 A | 10/2000 | Keller |
| 6,179,841 B1 | 1/2001 | Jackson |
| 6,189,422 B1 | 2/2001 | Stihl |
| 6,224,598 B1 | 5/2001 | Jackson |
| 6,251,112 B1 | 6/2001 | Jackson |
| 6,258,090 B1 | 7/2001 | Jackson |
| 6,379,356 B1 | 4/2002 | Jackson |
| 6,440,132 B1 | 8/2002 | Jackson |
| 6,440,133 B1 | 8/2002 | Beale |
| 6,485,494 B1 | 11/2002 | Haider |
| 6,530,929 B1 | 3/2003 | Justis |
| 6,554,834 B1 | 4/2003 | Crozet |
| 6,648,888 B1 | 11/2003 | Shluzas |
| 6,723,100 B2 | 4/2004 | Biedermann |
| 6,726,687 B2 | 4/2004 | Jackson |
| 6,743,231 B1 | 6/2004 | Gray |
| 6,884,244 B1 | 4/2005 | Jackson |
| 7,008,422 B2 | 3/2006 | Foley |
| 7,011,660 B2 | 3/2006 | Sherman |
| 7,073,415 B2 | 7/2006 | Casutt |
| 7,094,239 B1 | 8/2006 | Michelson |
| 7,160,300 B2 | 1/2007 | Jackson |
| 7,179,261 B2 | 2/2007 | Sicvol |
| 7,188,626 B2 | 3/2007 | Foley |
| 7,204,838 B2 | 4/2007 | Jackson |
| 7,250,052 B2 | 7/2007 | Landry |
| 7,278,995 B2 | 10/2007 | Nichols |
| D560,128 S | 1/2008 | Diederich |
| 7,470,279 B2 | 12/2008 | Jackson |
| 7,476,240 B2 | 1/2009 | Raymond |
| 7,491,208 B2 | 2/2009 | Pond |
| 7,491,218 B2 | 2/2009 | Landry |
| 7,520,879 B2 | 4/2009 | Justis |
| 7,527,638 B2 | 5/2009 | Anderson |
| 7,563,264 B2 | 7/2009 | Landry |
| 7,574,318 B2 | 8/2009 | Hsieh |
| 7,588,575 B2 | 9/2009 | Colleran |
| 7,588,588 B2 | 9/2009 | Spitler |
| 7,608,081 B2 | 10/2009 | Abdelgany |
| 7,618,422 B2 | 11/2009 | Goodwin |
| 7,621,918 B2 | 11/2009 | Jackson |
| 7,648,521 B2 | 1/2010 | Hestad |
| 7,651,502 B2 | 1/2010 | Jackson |
| 7,678,139 B2 | 3/2010 | Gararnszegi |
| 7,691,132 B2 | 4/2010 | Landry |
| 7,708,743 B2 | 5/2010 | Anderson |
| 7,708,763 B2 | 5/2010 | Selover |
| 7,717,921 B2 | 5/2010 | Rezach |
| 7,717,944 B2 | 5/2010 | Foley |
| 7,744,629 B2 | 6/2010 | Hestad |
| 7,749,233 B2 | 7/2010 | Farr |
| 7,758,617 B2 | 7/2010 | Iott |
| 7,763,055 B2 | 7/2010 | Foley |
| 7,771,430 B2 | 8/2010 | Jones |
| 7,811,288 B2 | 10/2010 | Jones |
| 7,854,751 B2 | 12/2010 | Sicvol |
| 7,862,595 B2 | 1/2011 | Foley |
| 7,887,259 B2 | 1/2011 | Foley |
| 7,909,835 B2 | 3/2011 | Oribe |
| 7,914,558 B2 | 3/2011 | Landry |
| 7,918,857 B2 | 4/2011 | Dziedzic |
| 7,918,858 B2 | 4/2011 | Stad |
| 7,918,878 B2 | 4/2011 | Songer |
| 7,922,727 B2 | 4/2011 | Songer |
| 7,927,334 B2 | 4/2011 | Miller |
| 7,931,673 B2 | 4/2011 | Hestad |
| 7,931,854 B2 | 4/2011 | Jones |
| 7,947,045 B2 | 5/2011 | Hestad |
| 7,955,355 B2 | 6/2011 | Chin |
| 7,967,821 B2 | 6/2011 | Sicvol |
| 7,985,242 B2 | 7/2011 | Forton |
| 8,002,798 B2 | 8/2011 | Chin |
| 8,034,084 B2 | 10/2011 | Landry |
| 8,052,720 B2 | 11/2011 | Kuester |
| 8,062,340 B2 | 11/2011 | Berrevoets |
| 8,066,739 B2 | 11/2011 | Jackson |
| 8,075,592 B2 | 12/2011 | Landry |
| 8,100,915 B2 | 1/2012 | Jackson |
| 8,100,951 B2 | 1/2012 | Justis |
| 8,105,361 B2 | 1/2012 | Anderson |
| 8,137,355 B2 | 3/2012 | Hestad |
| 8,137,356 B2 | 3/2012 | Hestad |
| 8,137,387 B2 | 3/2012 | Garamszegi |
| 8,152,810 B2 | 4/2012 | Jackson |
| 8,162,948 B2 | 4/2012 | Jackson |
| 8,177,817 B2 | 5/2012 | Fallin |
| 8,192,439 B2 | 6/2012 | Songer |
| 8,192,440 B2 | 6/2012 | Jones |
| 8,231,635 B2 | 7/2012 | Sharifi-Mehr |
| 8,262,662 B2 | 9/2012 | Beardsley |
| 8,273,089 B2 | 9/2012 | Jackson |
| 8,277,491 B2 | 10/2012 | Selover |
| 8,292,892 B2 | 10/2012 | Jackson |
| 8,303,505 B2 | 11/2012 | Jones |
| 8,308,728 B2 | 11/2012 | Iott |
| 8,317,796 B2 | 11/2012 | Stlhl |
| 8,361,124 B2 | 1/2013 | Sherman |
| 8,377,067 B2 | 2/2013 | Jackson |
| 8,460,300 B2 | 6/2013 | Hestad |
| 8,460,308 B2 | 6/2013 | Marino |
| 8,470,008 B2 | 6/2013 | Dickinson |
| 8,496,685 B2 | 7/2013 | Landry |
| 8,518,082 B2 | 8/2013 | Sicvol |
| 8,608,746 B2 | 12/2013 | Kolb |
| 8,617,427 B2 | 12/2013 | Jiang |
| RE44,813 E | 3/2014 | Beale |
| 8,663,298 B2 | 3/2014 | Keyer |
| 8,679,128 B2 | 3/2014 | Seelig |
| 8,821,502 B2 * | 9/2014 | Gleeson ............... A61B 17/708 606/105 |
| 9,066,763 B2 * | 6/2015 | Khoo .................... A61B 17/708 |
| 9,125,703 B2 * | 9/2015 | McClintock ........... A61B 17/88 |
| 9,198,698 B1 * | 12/2015 | Doose .................. A61B 17/708 |
| 9,974,577 B1 * | 5/2018 | Smith ................. A61B 17/7076 |
| 2002/0072751 A1 | 6/2002 | Jackson |
| 2002/0133159 A1 | 9/2002 | Jackson |
| 2003/0199872 A1 | 10/2003 | Markworth |
| 2003/0224327 A1 | 12/2003 | Constantino |
| 2003/0225408 A1 | 12/2003 | Nichols |
| 2003/0236529 A1 | 12/2003 | Shluzas |
| 2004/0039383 A1 | 2/2004 | Jackson |
| 2004/0049196 A1 | 3/2004 | Jackson |
| 2004/0147937 A1 | 7/2004 | Dunbar |
| 2004/0158247 A1 | 8/2004 | Sitiso |
| 2004/0167523 A1 | 8/2004 | Jackson |
| 2004/0254576 A1 | 12/2004 | Dunbar |
| 2004/0267275 A1 | 12/2004 | Cournoyer |
| 2005/0176468 A1 | 8/2005 | Iacono |
| 2005/0182410 A1 | 8/2005 | Jackson |
| 2005/0192570 A1 | 9/2005 | Jackson |
| 2005/0192579 A1 | 9/2005 | Jackson |
| 2005/0228380 A1 | 10/2005 | Moore |
| 2006/0036254 A1 | 2/2006 | Lim |
| 2006/0069391 A1 | 3/2006 | Jackson |
| 2006/0074418 A1 | 4/2006 | Jackson |
| 2006/0089651 A1 | 4/2006 | Trudeau |
| 2006/0095035 A1 | 5/2006 | Jones |
| 2006/0100622 A1 | 5/2006 | Jackson |
| 2006/0111712 A1 | 5/2006 | Jackson |
| 2006/0111713 A1 | 5/2006 | Jackson |
| 2006/0111715 A1 | 5/2006 | Jackson |
| 2006/0200132 A1 | 9/2006 | Chao |
| 2006/0229614 A1 | 10/2006 | Foley |
| 2006/0247630 A1 | 11/2006 | Iott |
| 2006/0276789 A1 | 12/2006 | Jackson |
| 2006/0293684 A1 | 12/2006 | Shluzas |
| 2006/0293692 A1 | 12/2006 | Whipple |
| 2007/0043378 A1 | 2/2007 | Kumar |

(56) References Cited

U.S. PATENT DOCUMENTS

| | | |
|---|---|---|
| 2007/0055240 A1 | 3/2007 | Matthis |
| 2007/0065692 A1 | 3/2007 | Ryoo |
| 2007/0213722 A1 | 9/2007 | Jones |
| 2007/0270811 A1 | 11/2007 | Dewey |
| 2007/0288002 A1 | 12/2007 | Carls |
| 2007/0288007 A1 | 12/2007 | Burkus |
| 2007/0299450 A1 | 12/2007 | Her |
| 2008/0009864 A1 | 1/2008 | Forton |
| 2008/0015601 A1 | 1/2008 | Castro |
| 2008/0039844 A1 | 2/2008 | Jackson |
| 2008/0045957 A1 | 2/2008 | Wagner |
| 2008/0045970 A1 | 2/2008 | Saidha |
| 2008/0051794 A1 | 2/2008 | Dec |
| 2008/0077155 A1* | 3/2008 | Diederich ............ A61B 17/708 606/105 |
| 2008/0086132 A1 | 4/2008 | Biedermann |
| 2008/0091213 A1 | 4/2008 | Jackson |
| 2008/0172062 A1 | 7/2008 | Donahue |
| 2008/0234678 A1 | 9/2008 | Gutierrez |
| 2008/0243190 A1 | 10/2008 | Dziedzic |
| 2008/0275456 A1 | 11/2008 | Vonwiller |
| 2008/0288005 A1 | 11/2008 | Jackson |
| 2008/0300638 A1 | 12/2008 | Beardsley |
| 2009/0030419 A1 | 1/2009 | Runco |
| 2009/0030420 A1 | 1/2009 | Runco |
| 2009/0105712 A1 | 4/2009 | Dauster |
| 2009/0157125 A1 | 6/2009 | Hoffman |
| 2009/0174467 A1 | 7/2009 | Kim |
| 2009/0216281 A1 | 8/2009 | Vonwiller |
| 2009/0216328 A1 | 8/2009 | Birkmeyer |
| 2009/0228053 A1 | 9/2009 | Kolb |
| 2009/0228054 A1 | 9/2009 | Hoffman |
| 2009/0228055 A1 | 9/2009 | Jackson |
| 2009/0240292 A1 | 9/2009 | Butler |
| 2009/0254125 A1 | 10/2009 | Predick |
| 2009/0275994 A1 | 11/2009 | Phan |
| 2009/0306721 A1 | 12/2009 | Kirschman |
| 2010/0004696 A1 | 1/2010 | Jackson |
| 2010/0036434 A1 | 2/2010 | Ely |
| 2010/0057126 A1 | 3/2010 | Hestad |
| 2010/0063552 A1 | 3/2010 | Chin |
| 2010/0121385 A1 | 5/2010 | Blain |
| 2010/0137991 A1 | 6/2010 | Ainsworth |
| 2010/0160921 A1 | 6/2010 | Sun |
| 2010/0238572 A1 | 9/2010 | Tao |
| 2010/0292742 A1 | 11/2010 | Stad |
| 2010/0294595 A1 | 11/2010 | Osburn |
| 2010/0331901 A1 | 12/2010 | Iott |
| 2011/0004222 A1 | 1/2011 | Biedermann |
| 2011/0034961 A1 | 2/2011 | Runco |
| 2011/0040328 A1 | 2/2011 | Miller |
| 2011/0040335 A1 | 2/2011 | Stihl |
| 2011/0077692 A1 | 3/2011 | Jackson |
| 2011/0087293 A1 | 4/2011 | Ferreira |
| 2011/0106187 A1 | 5/2011 | Foley |
| 2011/0137358 A1 | 6/2011 | Manninen |
| 2011/0184469 A1 | 7/2011 | Ballard |
| 2011/0202137 A1 | 8/2011 | Keith |
| 2011/0218583 A1 | 9/2011 | Smith |
| 2011/0234466 A1 | 9/2011 | Yamada |
| 2011/0238117 A1 | 9/2011 | Geist |
| 2011/0257692 A1 | 10/2011 | Sandstrom |
| 2011/0282402 A1 | 11/2011 | Chao |
| 2012/0016425 A1 | 1/2012 | Shaffrey |
| 2012/0078316 A1 | 3/2012 | Anderson |
| 2012/0100497 A1 | 4/2012 | Joo |
| 2012/0123431 A1 | 5/2012 | Robinson |
| 2012/0158070 A1 | 6/2012 | Jackson |
| 2012/0165876 A1 | 6/2012 | Nichols |
| 2012/0191144 A1 | 7/2012 | Peultier |
| 2012/0203288 A1 | 8/2012 | Lange |
| 2012/0271365 A1 | 10/2012 | Daubs |
| 2012/0277800 A1 | 11/2012 | Jackson |
| 2013/0035728 A1 | 2/2013 | Jackson |
| 2013/0035729 A1 | 2/2013 | Hammer |
| 2013/0072987 A1 | 3/2013 | Justis |
| 2013/0090697 A1 | 4/2013 | George |
| 2013/0110124 A1 | 5/2013 | Gleason |
| 2013/0110184 A1* | 5/2013 | Wing .................. A61B 17/708 606/86 A |
| 2013/0184763 A1 | 7/2013 | McClintock |
| 2013/0296949 A1 | 11/2013 | Sicvol |
| 2013/0296950 A1 | 11/2013 | Landry |
| 2013/0304130 A1 | 11/2013 | Jackson |
| 2014/0031872 A1 | 1/2014 | Jackson |
| 2014/0031873 A1 | 1/2014 | Jackson |
| 2014/0039567 A1 | 2/2014 | Hoefer |
| 2014/0058465 A1 | 2/2014 | Nichols |
| 2014/0074106 A1 | 3/2014 | Shin |
| 2014/0100613 A1 | 4/2014 | Iott |
| 2014/0100617 A1 | 4/2014 | Sandstrom |
| 2014/0100618 A1 | 4/2014 | Kolb |
| 2014/0107708 A1 | 4/2014 | Biedermann |
| 2014/0163625 A1 | 6/2014 | Meyer |
| 2014/0194939 A1 | 7/2014 | Seelig |

FOREIGN PATENT DOCUMENTS

| | | |
|---|---|---|
| EP | 1839606 | 11/2008 |
| EP | 234787 A1 | 5/2011 |
| EP | 2070485 | 9/2011 |
| EP | 2462889 A1 | 6/2012 |
| EP | 2574297 A1 | 4/2013 |
| EP | 2719347 A1 | 4/2014 |
| FR | 2920663 A1 | 3/2009 |
| JP | 2003265492 A | 9/2003 |
| WO | WO-02094114 A1 | 11/2002 |
| WO | WO-2012127267 | 9/2012 |
| WO | WO-2012127268 | 9/2012 |

* cited by examiner

METHODS AND INSTRUMENTS FOR PERFORMING LEVERAGED REDUCTION DURING SINGLE POSITION SPINE SURGERY

CROSS-REFERENCES TO RELATED APPLICATIONS

The present application is a continuation of U.S. patent application Ser. No. 15/158,925, filed May 19, 2016 (the contents being incorporated herein by reference), which claims priority from U.S. Provisional Patent Application Ser. No. 62/165,078, filed May 21, 2015 (the contents being incorporated herein by reference).

FIELD

This application describes methods and instruments for performing surgical maneuvers across one or more segments of the spinal column. More particularly, the surgical maneuvers are performed on the anterior column and posterior column of the spine with the patient positioned in the lateral decubitus position.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease or trauma, such as ruptured or slipped discs, degenerative disc disease, fractured vertebrae, and the like. Patients that suffer from such conditions usually experience extreme and debilitating pain, as well as diminished nerve function.

A noteworthy trend in the medical community is the move away from performing surgery via traditional, "open" techniques in favor of "minimally invasive" or "minimal access" techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called minimal access and minimally invasive techniques) are gaining favor due to the fact that they involve accessing surgical target sites via incisions of substantially smaller size with greatly reduced tissue displacement requirements. This, in turn, reduces the pain, morbidity, and cost associated with such procedures. One such minimally invasive approach, a lateral trans-psoas approach to the spine, developed by NuVasive®, Inc., San Diego, Calif. (XLIF®) has demonstrated great success in reducing patient morbidity, shortening the duration of hospitalization, and speeding recovery time if it is employed.

In some instances, it is desirable to perform a lateral lumbar interbody fusion procedure with supplemental posterior fixation. This may require re-positioning the patient from the lateral decubitus position to the prone position which can significantly increase operative time among other things. It is therefore advantageous to perform so-called "single position spine surgery" in which the lateral lumbar interbody fusion procedure and the posterior fixation procedure are performed while maintaining the patient in the lateral decubitus position. In some instances, patient pathology (for example, spondylolisthesis) presents significant challenges to single position spine surgery. What is needed are methods and instruments that facilitate single position surgery in a wide variety of pathologies. The present invention addresses the aforementioned needs.

SUMMARY OF THE INVENTION

In one aspect of the invention, a spinal procedure comprises attaching a first reduction instrument to a first guide assembly and a second guide assembly; attaching the first guide assembly to a first pedicle; attaching the second guide assembly to a second pedicle; moving the first reduction instrument to reduce an orientation of the spine; and following the reduction of the orientation of the spine, at least one of inserting an interbody implant into the spine and attaching a rod to the spine.

In a further aspect of the invention, a spinal procedure comprises attaching a first reduction instrument to a pair of first guide assemblies; attaching a second reduction instrument to a pair of second guide assemblies; attaching the first guide assemblies to upside pedicles; attaching the second guide assemblies to downside pedicles; moving the first reduction instrument to reduce an orientation of the spine; locking an angle and position of the first reduction instrument upon achieving a desired reduction; and following the desired reduction, at least one of inserting an interbody implant into the spine and attaching a rod to the spine.

In yet another aspect of the invention, a spinal reduction instrument comprises a body having: a pair of racks; and translational slots in the racks; a fixed attachment assembly pivotally attached to the racks, wherein the fixed attachment assembly is configured to: prevent rotation thereof relative to the body; and engage a first guide assembly; a translating attachment assembly pivotally attached to the racks, wherein the translating attachment assembly is configured to: translate in the translational slots; and engage a second guide assembly.

These and other features, aspects and advantages of the present invention will become better understood with reference to the following drawings, description and claims.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and instruments disclosed herein boast a variety of inventive features and components that warrant patent protection, both individually and in combination.

Broadly, the present invention provides methods and apparatus for spinal surgical procedures. Some exemplary methods include lateral lumbar interbody fusion procedures and posterior fixation procedures. In exemplary procedures, the patient is maintained in a lateral decubitus position.

In order to gain direct physical and fluoroscopic access to bilateral posterior anatomy, it is helpful to position the patient appropriately at the onset of the case. In an embodiment, the patient can be centered on the table in an anterior-posterior direction, with the greater trochanter of the patient positioned at the table break. Next, the patient can be rolled slightly in the anterior direction, such as approximately 15 degrees. By way of example only, this may be measured at the intercrestal line with a digital protractor or virtual plumb line (e.g., via a smartphone app). The patient may then be secured to the OR table (e.g., with surgical tape). The bed can then be tilted in the posterior direction to counter act the forward roll of the patient until a true anterior/posterior (AP) fluoroscopic image is obtained.

After the patient is oriented and secured in the desired position, the surgical levels and skin approach can be localized. According to an exemplary implementation, AP fluoroscopy can be used to find the midline at the spinous process and the skin is marked, such as about 5.5 cm above and below that point with longitudinal lines (such as for a Wiltse paramedial approach). Lateral fluoroscopic images may then be used to determine cephalad/caudal angles through the pedicles and this line may be projected posteriorly to intersect the Wiltse lines. Once completed for the upper and lower spinal levels of the surgical procedure, the exact skin approach is known and the surgical procedure may commence.

According to a first exemplary embodiment, a lateral lumbar interbody fusion procedure (by way of example only, an XLIF® procedure) may be performed followed by posterior fixation (by way of example only, bilateral pedicle screw fixation via open, percutaneous, and minimally invasive techniques) while the patient remains in the lateral decubitus position. According to one exemplary implementation (described below) posterior fixation may be effectuated utilizing a minimally invasive posterior fixation system.

For purposes of illustration, systems and methods of the present invention will be described for use in conjunction with a minimally invasive posterior fixation system utilized with a patient positioned in the lateral decubitus position. It is to be appreciated, however, that such systems and techniques are contemplated for use with open as well as percutaneous posterior fixation systems as well.

Bilateral Pedicle Screw Instrumentation in the
Lateral Decubitus Position Using Biplanar
Fluoroscopy Bilateral pedicle screws may be placed in the lateral decubitus position using a biplanar, or anterior-posterior, fluoroscopic view of the pedicles. Using the previously mapped and marked Wiltse incisions, incisions can be made, tissue can be retracted (e.g., with a Wheatlaner retractor), the fascia can be divided, and the facet and transverse processes can be located using blunt finger dissection. A pedicle access instrument 10 (FIG. 1) (e.g., a NuVasive® IPAS™ instrument) may mate with a complimentary clip feature on a posterior face of an orthogonal tilt sensor adaptor. The instrument 10 may include a handle 10, a handle post 12, and a tip 13. The tip 13 may be delivered to a surgical target site (e.g., the sulcus of the transverse process and the superior articular process junction). A lateral fluoroscopic image may be taken to: 1) localize the target spinal level; 2) assess the angles of approach; and 3) evaluate depth at the tip of the localizing instrument. Adjustments and additional localizing fluoroscopic x-ray shots may be made until the desired starting point is confirmed. This confirmation x-ray may be used to ensure that the C-arm is aligned with the endplate of the target spinal level.

Figure 1:
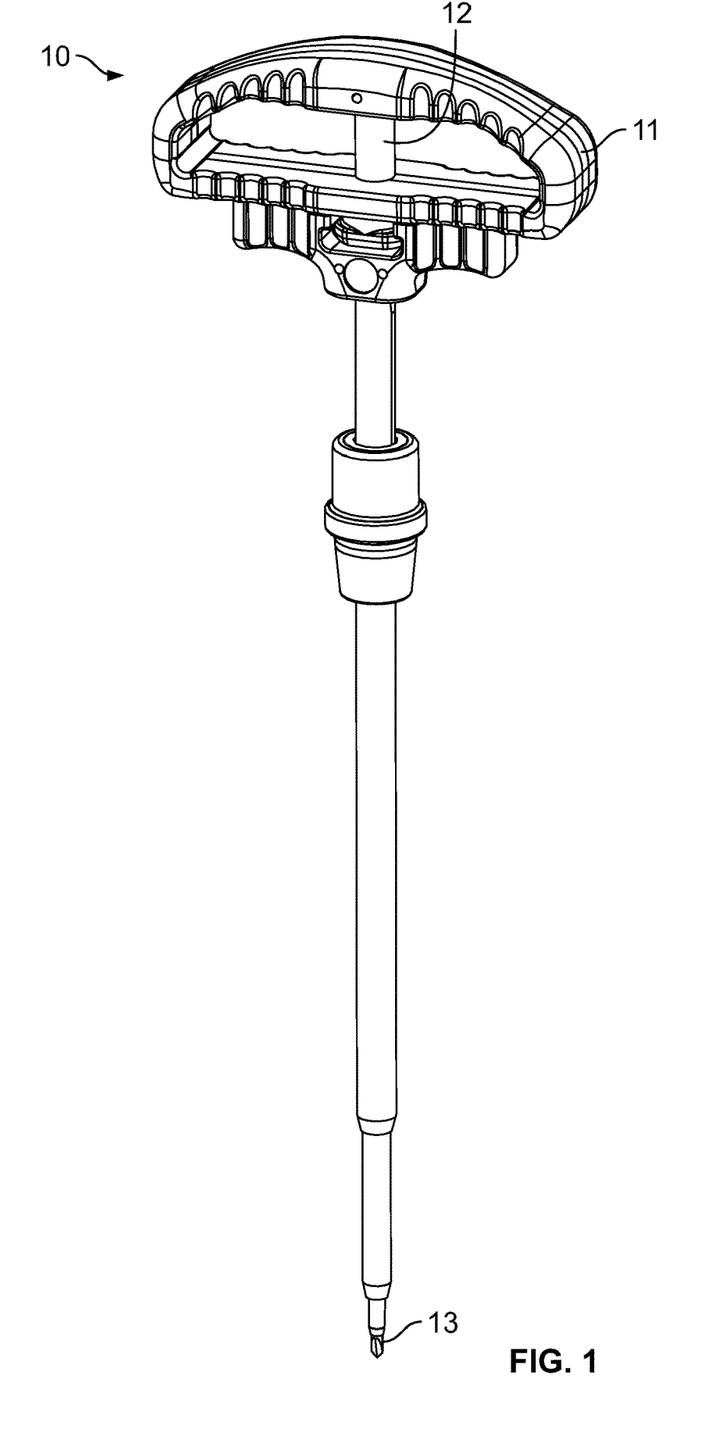
FIG. 1 is a perspective view of a pedicle access instrument for use with a navigated guidance system according to one embodiment.

If satisfied, the pedicle access instrument 10 may be tapped into position to set the tip 13, and the C-arm may be moved to the A/P position to take an AP image. If, in the A/P position, the tip 13 is positioned on the lateral aspect of the pedicle and on/near the 9 o'clock position (i.e., the upside or contralateral pedicle as it relates to the surface of the OR bed) or on/near the 3 o'clock position (i.e., the downside or ipsilateral pedicle), the tip may be advanced until it is at least fully engaged with the cortex of the bone. The C-arm may then be repositioned to the lateral position and the pedicle access instrument 10 may be advanced into the pedicle.

Figure 2:
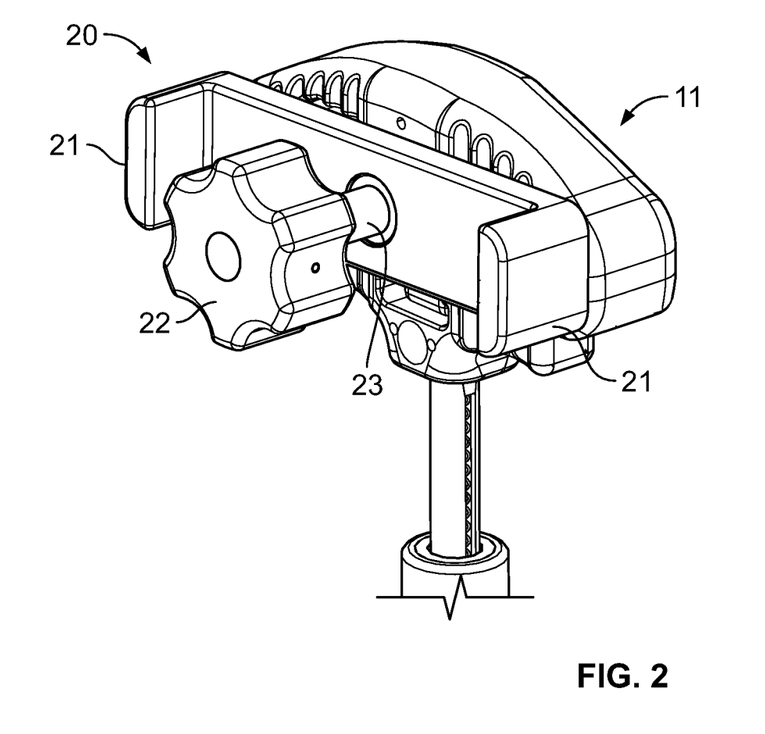
FIG. 2 is a perspective view of an orthogonal tilt sensor adaptor coupled to the pedicle access instrument of FIG. 1.
Figure 3:
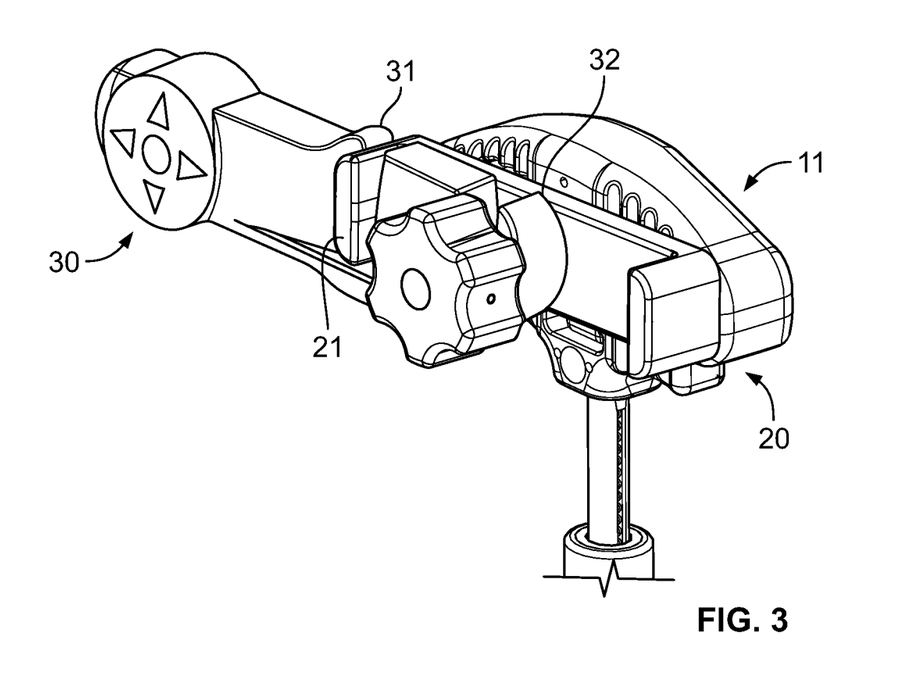
FIG. 3 is a perspective view of an orthogonal tilt sensor adaptor coupled to the assembly of FIG. 2.

According to one or more exemplary implementations, it is contemplated that the techniques described herein may be used with a navigated guidance system (e.g. NuVasive® Guidance™). The navigated guidance system may include one or more orthogonal tilt sensor adapters 20 (FIGS. 2-3). The adaptor 20 can include one or more securing arms 21, a securing knob 22, and a central post 23. The orthogonal tilt sensor adaptor 20 may orient a tilt sensor with respect to gravity while surgical instruments (e.g., pedicle access instrument, tap, screw driver, C-arm, etc.) are used on the posterior column of the spine with the patient positioned in the lateral decubitus position (FIGS. 1-5). Using the navigated guidance system, the cranial/caudal trajectory may be adjusted to ideal, and the tilt sensor may be used to set the medial/lateral angle to the templated angle.

Once the pedicle access instrument 10 has advanced to the desired depth (e.g., 30 mm), a stylet may be removed and a guide wire may be advanced to the desired depth. This process can be repeated on the contralateral pedicle of the same level and then advanced to the next level; however, it is contemplated that the process may be repeated in any order. Once all guide wires are in place, an AP image may be obtained to confirm angles match the expectation of convergence.

In FIG. 3, a tilt sensor clip 30, having a tilt sensor therein, may engage the adaptor 20 and may include a securing arm receiver 31 and an end hook 32. To secure the sensor clip 30 to the pedicle access instrument 10, the sensor clip 30 can be dimensioned to snugly receive at least a portion of the pedicle access instrument 10. By way of example, a fastener end of the clip 30 may comprise the end hook 32 and the securing arm receiver 31. To maintain a snug fit with the pedicle access instrument 10, the end hook 32 can be configured to snap on and tightly grasp a central post 23 of the orthogonal tilt sensor adapter 20. Thereafter, the sensor clip 30 can be rotated until the securing arm receiver 31 fully engages with the orthogonal tilt sensor adapter 20.

FIG. 3 illustrates the handle 11 of the instrument 10 engaged with the adapter 20 and the adapter 20 engaged with the sensor clip 30 after the sensor clip 30 has been rotated into position with the securing arm 21 engaged within the securing arm receiver 31. The sensor clip 30 can be dimensioned to prevent, once it is fully engage, the unintentional disengagement of the pedicle access instrument 10. When engaged, the sensor clip 30 may extend perpendicular to the longitudinal axis of the instrument 10 and parallel to the face of the handle 11. It is to be appreciated that, in such an orientation, the tilt sensor in the clip 30 maintains its position with respect to gravity while the pedicle access instrument 10 is used and while the patient is positioned in the lateral decubitus position.

Figures 4A, 4B, 4C:
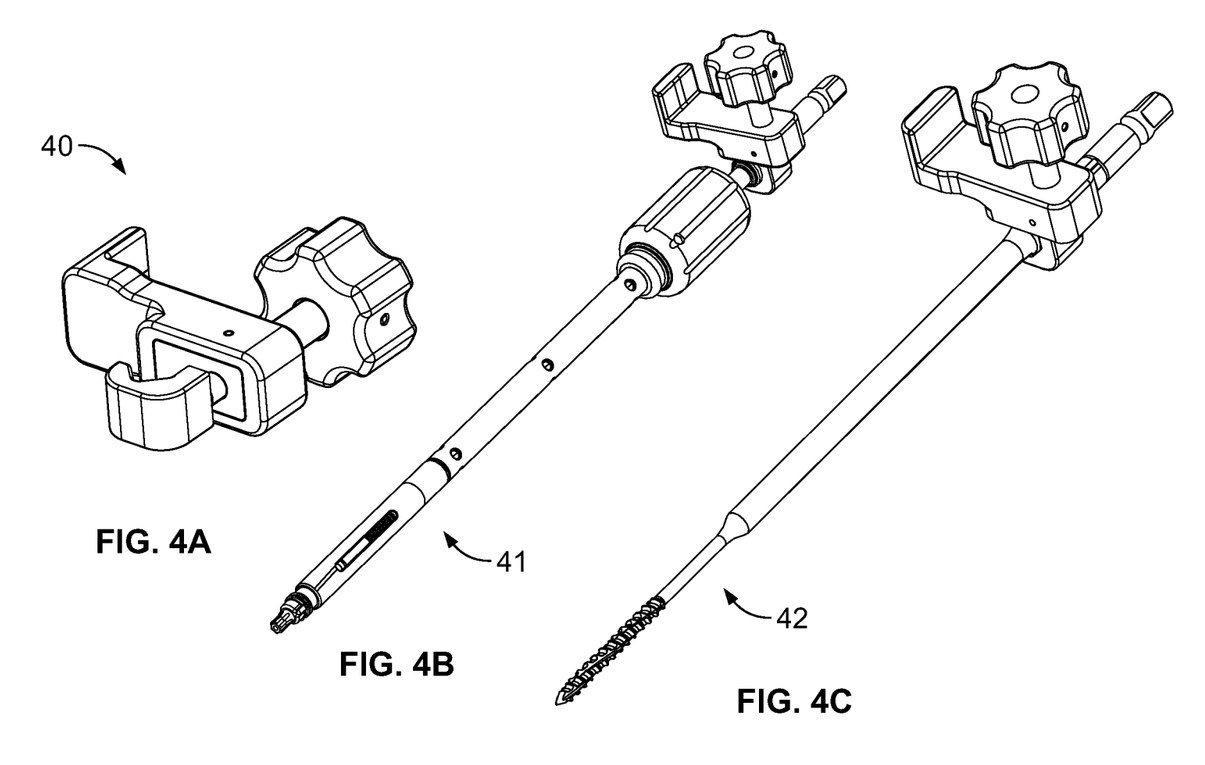
FIGS. 4A-D depicts a plurality of orthogonal tilt sensor adaptors for use with a navigated guidance system according to one embodiment.
Figure 4D:
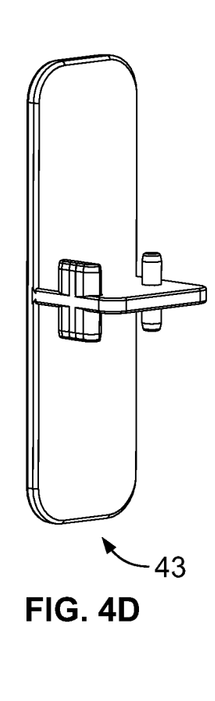

In FIGS. 4A-4C, another orthogonal tilt sensor adapter 40 is shown. The adaptor 40 may include a clamp 40a to enable the adaptor 40 to be affixed to a screwdriver 41 (FIG. 4B) or to a tap 42 (FIG. 4C). The orthogonal tilt sensor adaptor 40 may also employ a sensor clip adaptor 43 (FIG. 4D).

Figures 5A, 5B, 5C:
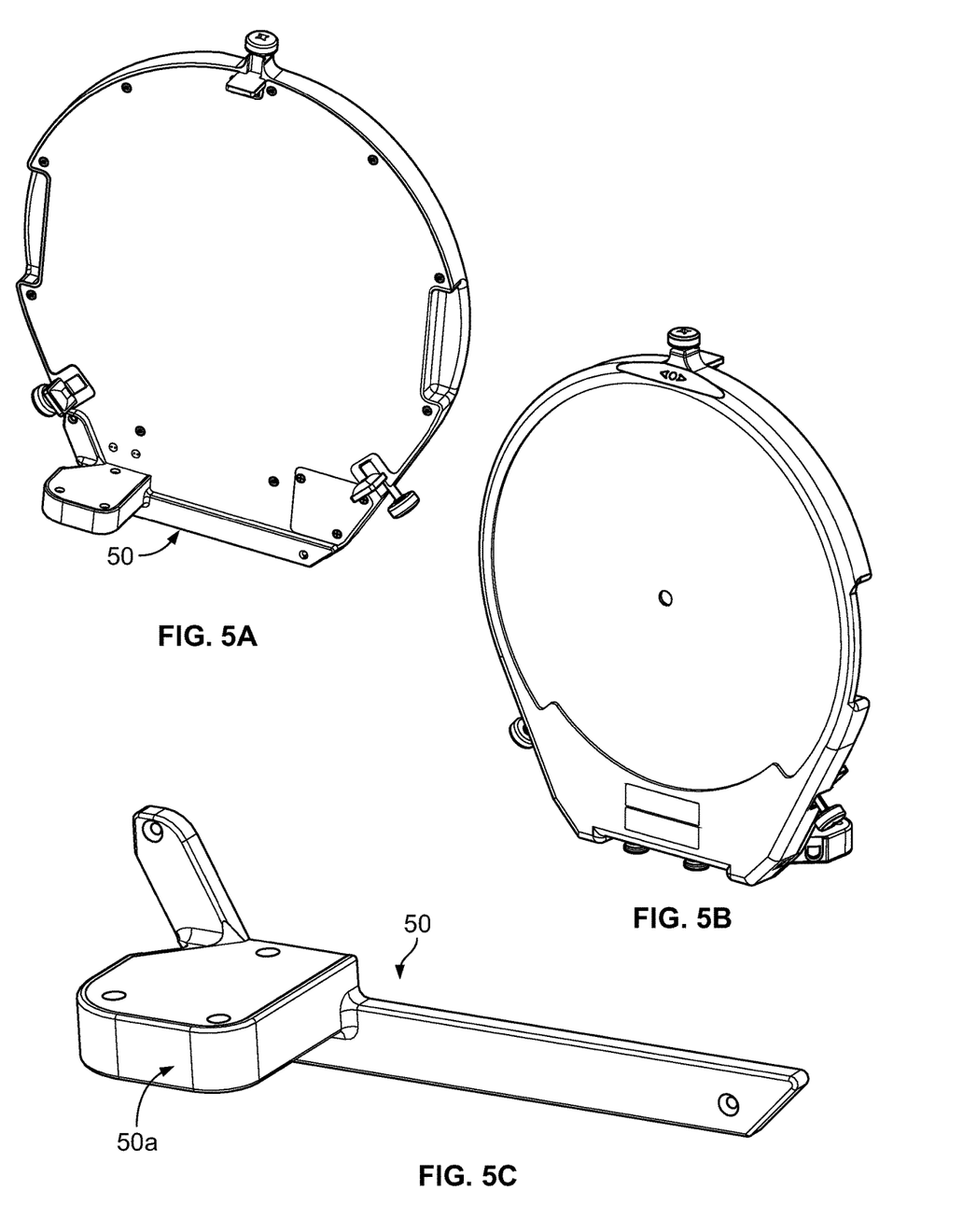
FIGS. 5A-C are plan views of an orthogonal tilt sensor adaptor coupled to a C-arm unit for use with a navigated guidance system according to one embodiment.

FIGS. 5A-5C depict another embodiment of orthogonal tilt sensor adaptor 50 with an integrated tilt sensor 50a. In FIG. 5A, a C-arm laser reticle with an attached orthogonal tilt sensor adaptor 50 is depicted. FIG. 5B is another view of the C-arm laser reticle with an attached orthogonal tilt sensor adaptor 50. The foregoing enables a user to utilize an "over-the-top" C-arm view.

In accordance with exemplary embodiments, with the C-arm in the lateral position, the pedicle angle may then be matched to the navigated guidance system feedback and the tap may be advanced into the pedicle. The tilt sensor clip may then be attached to a screwdriver via a screw driver adapter and the screwdriver may be advanced into the pedicle until the final desired depth is achieved. According to some implementations, the steps of preparing a pilot hole, advancing a tap, and placing a pedicle screw may be performed in conjunction with intraoperative neuromonitoring techniques, for example dynamic or basic screw stimulation using, by way of example only, a NuVasive® NVM5® intraoperative neurophysiologic monitoring device. The remainder of the posterior spinal fixation procedure may be completed per specific technique.

Figure 6A:
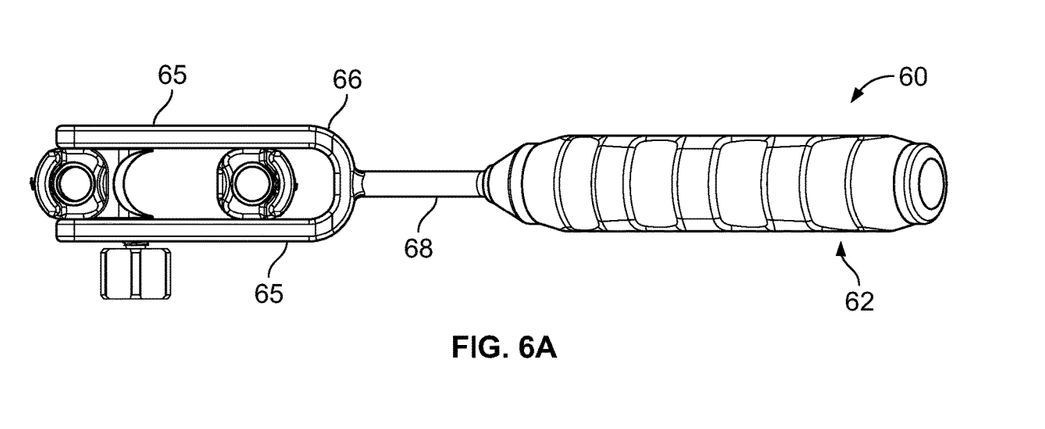
FIGS. 6A-D depict a reduction tool according to one embodiment.
Figure 6B:
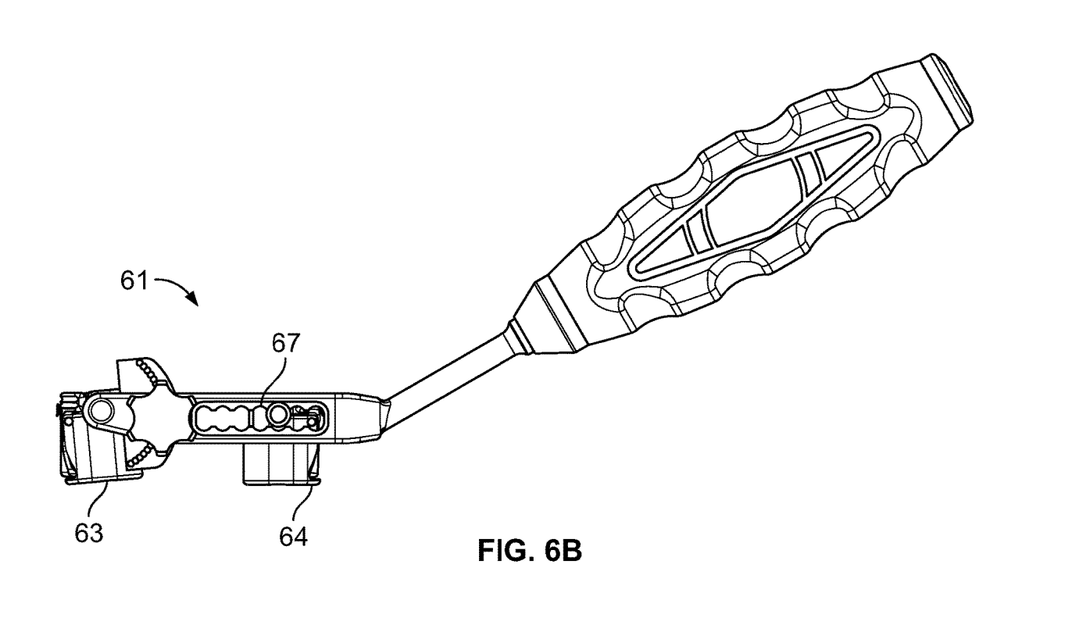

Once the pedicle screws have been properly seated, a reduction instrument 60 (FIGS. 6A-6D) can be employed. The reduction instrument 60 may be used for reduction in a single-level construct (i.e., two spinal levels). By way of example only, the reduction instrument may include a body 61, a handle 62, a fixed attachment assembly 63, and a translating attachment assembly 64 (FIGS. 6A-6B). The body 61 may include a pair of elongated racks 65 arranged parallel to one another and joined at a proximal end by a generally curved connector 66. The racks 65 can each include a translation slot 67 configured to allow the translating attachment assembly 64 to translate freely in both the proximal and distal directions. Each translation slot 67 may include a plurality of rounded openings configured to allow the translating attachment assembly 64 to rest in a single selected position without inhibiting the overall ability to translate. The handle 62 can be connected to the curved connector 66 via a shaft 68.

Figure 6C:
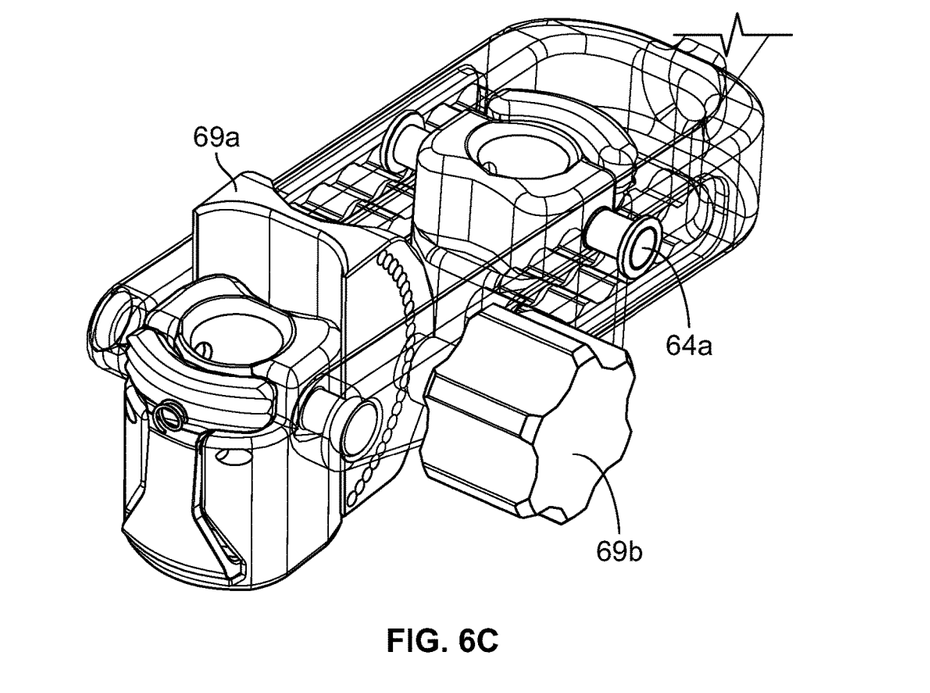

The fixed attachment assembly 63 can be positioned between the distal ends of each of the racks 65 and can be pivotably attached to each rack via a swivel pin 63a (FIG. 6C). The translating attachment assembly 64 can be positioned between the racks 65 and may be capable of freely translating therealong. The translating attachment assembly 64 may include a swivel pin 64a extending therethrough and have circular ends that engage the translation slot 67 and rest in the rounded openings 67a thereof. The fixed attachment assembly 63 and the translating attachment assembly 64 may each comprise a respective connector 63b, 64b that may attach to a respective guide assembly 70 (FIGS. 7A-7B) (via a cap).

Figure 6D:
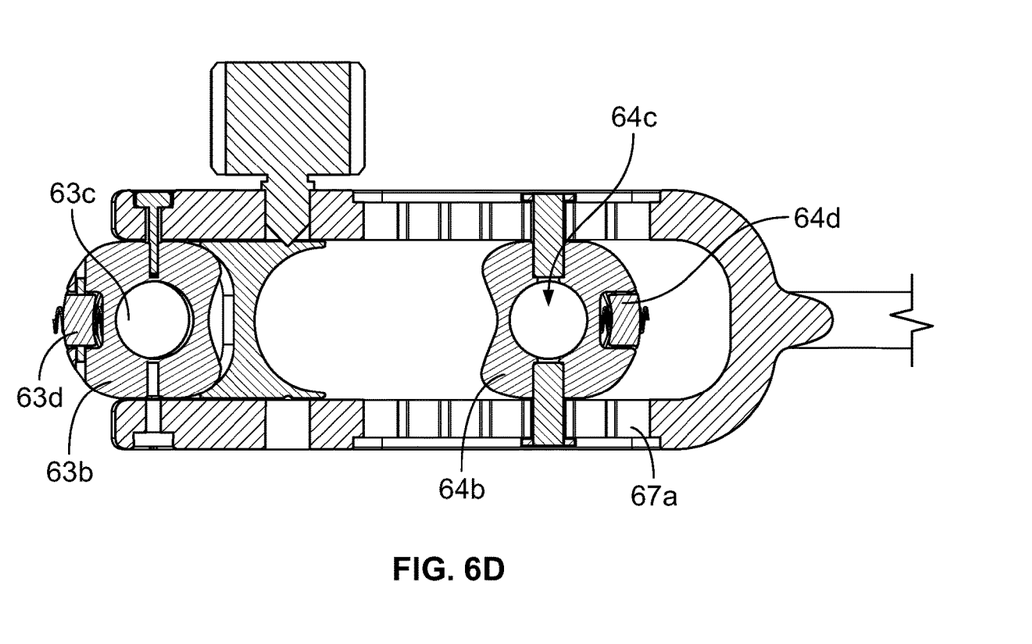

Each connector 63b, 64b can have a respective guide cavity 63c, 64c into which a proximal end of a respective guide assembly can be received (FIG. 6D). The proximal end of the guide assembly can be keyed to the guide cavity so as to prevent rotation of the guide assembly relative to the reduction instrument 60. Spring locks 63d, 64d on the connectors 63b, 64b may be provided to prevent translation of the guide assembly relative to the reduction instrument 60. According to one embodiment, the spring locks 63d, 64d can include ridges that extend through the connector into the guide cavity and engage a circumferential groove situated below the proximal end of the guide assembly when the guide assembly is mated with the reduction instrument. The ridges can allow the proximal end of the guide assembly to push past the spring locks until the ridges snap into place within the circumferential groove.

Adjacent to the fixed attachment assembly 63 can be a locking assembly 69. The locking assembly can be comprised of an angular body 69a and a thumbwheel 69b. The angular body 69a can be carried between the parallel racks 65 and may be attached to the connector of the fixed attachment assembly. In an embodiment, the fixed attachment assembly 63 and the locking assembly 69 are in a fixed relationship (e.g. via welding) with one another such that as the fixed attachment assembly moves about the swivel pin 64a, the angular body 69a moves with it. The angular body can include two outwardly facing lateral sides, at least one of which may include a plurality of dimples arranged in a generally-arced fashion. The thumbwheel 69b of the locking assembly can be threaded and include a tip that is sized and dimensioned for disposal through the rounded openings 67a on the parallel rack 65 and into one dimple of the angular body 69a. Tightening the thumbwheel 69b can lock the fixed attachment assembly 63 into one position.

Figures 7A, 7B:
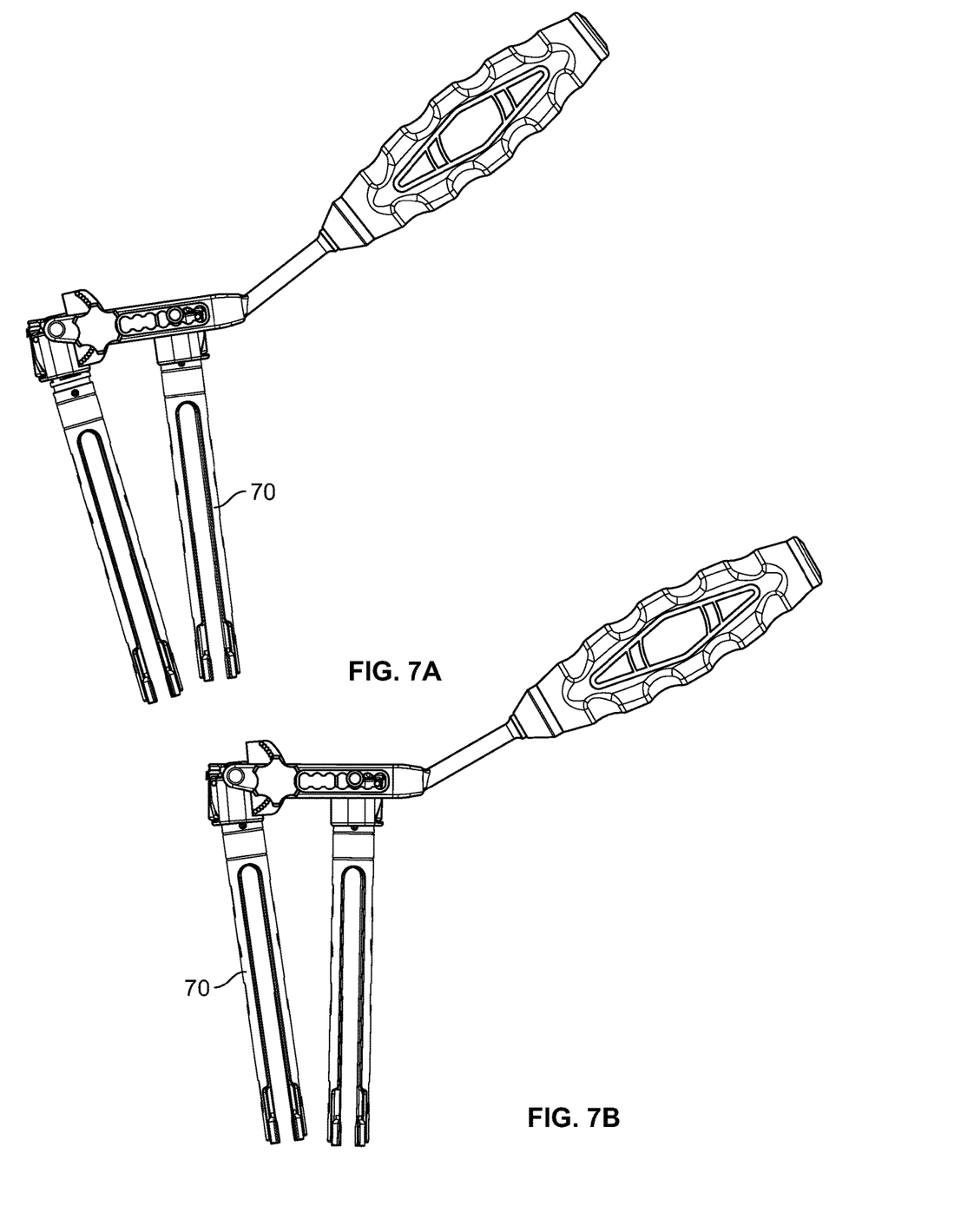
FIG. 7A depicts the reduction tool of FIGS. 6A-D attached to two guide assemblies, with the two guide assemblies in an unreduced configuration.
FIG. 7B depicts the reduction tool and guide assemblies of FIG. 7A, with the two guide assemblies in a reduced configuration.

FIG. 7A depicts the relative orientation of two reduction towers (i.e., guide assemblies) attached to two pedicle screws/vertebrae (not shown) prior to reduction of spondylolisthesis. FIG. 7B depicts the relative orientation of two reduction towers attached to two pedicle screws/vertebrae (not shown) following reduction of spondylolisthesis.

In use, the reduction instrument 60 (with the locking assembly 69 in an unlocked configuration) can be attached, via the fixed attachment assembly 63, to a first guide assembly 70 at a first vertebral level, and can be attached, via the translating attachment assembly 64, to a second guide assembly 70 on an adjacent vertebral level. The attachment assemblies 63, 64 can be attached to the guide assemblies in the manner described above. The handle 62 may then pushed downward (e.g., toward the spine), causing the body 61 of the reduction instrument 60 to pivot around the translating attachment assembly 64, thereby lifting the fixed translation assembly 63. Thus, the screw, the guide, and ultimately the vertebra can be lifted upward (i.e., reduced) to the desired position. Once in the desired position, the thumbwheel 69b of the locking assembly 69 can be tightened until the pin firmly seats into the dimple corresponding to the desired angular position of the fixed attachment assembly (i.e., reduction correction). This can secure the reduction in place while the lateral lumbar interbody implant and spinal rods are placed. A lock screw can be introduced via a lock screw inserter (not shown) and attached to the pedicle screw. The reduction instrument 60 can then be removed and the lock screw tightened via a final tightening device (not shown).

Bilateral Pedicle Screw Instrumentation in the Lateral Decubitus Position Using Oblique Fluoroscopy Bilateral pedicle screws can be placed in the lateral decubitus position using an oblique, or en fasse, fluoroscopic view of the pedicles. If the oblique view is intended, it is advantageous to flip the C-arm to an "over-the-top" configuration so that both pedicles (pedicles ipsilateral and contralateral to the bed surface) can be viewed in the oblique projection.

The patient positioning and preparation steps can be the same as discussed above and, as such, will not be repeated here.

Downside pedicles can be targeted first, again having measured and marked the Wiltse incision previously. After confirming true lateral patient position, the orthogonal C-arm reticle tilt sensor can be used to align the C-arm to the templated pedicle angle. Images can be taken with a radiopaque marker on the skin directly over the pedicle, and proper visualization can be confirmed.

Using the previously mapped and marked Wiltse incisions, incisions can be made, tissue can be retracted (e.g., with a Wheatlaner retractor), the fascia can be divided, and the facet and transverse processes can be located using blunt finger dissection. The tip of a pedicle access instrument (e.g., a NuVasive® IPAS™ instrument) may be delivered to a surgical target site (e.g., the sulcus of the transverse process and the superior articular process junction) such that an oblique fluoroscopic image may be taken to: 1) localize the target spinal level; 2) assess the angles of approach; and 2) evaluate depth at the tip of the localizing instrument. Adjustments and additional localizing fluoroscopic x-ray shots may be made until the desired starting point is confirmed. Next, the C-arm may be brought to lateral position.

Once the pedicle access instrument has advanced to the desired depth (e.g., 30 mm), the stylett may be removed, and a guide wire may be advanced to the desired depth. This process can be repeated on all of the ipsilateral screws until all of the levels are cannulated with guide wires before moving on to contralateral pedicles.

To properly visualize the upside (contralateral) pedicles, the C-arm can be reversed at the joints to enable "over-the-top" orientation. To ensure sterility of the C-arm, a tunnel C-arm drape can be connected to a ¾ drape with Ioban. The sheet can then be clamped to the drapes at the level of the lateral aspect of the patient to provide a sterile barrier for the arc of the C-arm. The C-arm then arcs over the patient to the templated pedicle angle, as measured by the orthogonal C-arm reticle tilt sensor. The guide wires can be placed in a similar fashion as described above with respect to the down side pedicles and repeated until all pedicles are cannulated and guide wires are placed. Once all guide wires are in place, AP and lateral images may be obtained to confirm angles match the expectation of convergence.

The tilt sensor clip may then be attached to a tap via a tap adapter. With the C-arm in the lateral position, the pedicle angle may then be matched to the navigated guidance system feedback and the tap may be advanced into the pedicle. The tilt sensor clip may then be attached to a screwdriver via a screw driver adapter and the screwdriver may be advanced into the pedicle until the final desired depth is achieved. According to some implementations, the steps of preparing a pilot hole, advancing a tap, and placing a pedicle screw may be performed in conjunction with intraoperative neuromonitoring techniques, for example dynamic or basic screw stimulation using, by way of example only, a NuVasive® NVM5® intraoperative neurophysiologic monitoring device. The remainder of the posterior spinal fixation procedure may be completed per specific technique.

Leveraged Reduction Prior to Cage Placement

According to another embodiment, pedicle screws may be placed in a minimally invasive fashion prior to the lateral lumbar interbody fusion procedure with the remainder of the posterior spinal fixation procedure. One advantage of such a methodology is the ability to reduce a spondylolisthesis from the lateral decubitus position leveraging pedicle screws.

The patient positioning, C-arm orientation, and incision mapping steps may be performed in the manner as set forth above or any other manner known in the art. All pedicle screws may then be placed at the desired levels. This may be done using one of the bilateral or oblique fluoroscopy techniques described above.

According to one exemplary implementation, with the C-arm placed in the lateral position, the reduction instrument (described in regards to FIGS. 6A-D and 7) may be attached to the superior and inferior guide assemblies 70 attached to the "upside" pedicles. In some instances, it may be desirable to attach a second reduction instrument (which may be the same as the reduction instrument described wherein) to the superior and inferior guide assemblies attached to the "downside" pedicles. Fluoroscopic images may then be taken as the reduction instruments are maneuvered to visualize reduction of the spondylolisthesis. Once the desired reduction is complete, the set screw of the reduction instrument may be locked as described below. C-arm fluoroscopy may be used periodically to verify that the desired amount of reduction remains unchanged. With the reduction tool locked at the desired angle and position, the lateral lumbar interbody fusion portion of the procedure may be performed according to surgeon preference and may include manual reduction of the spondylolisthesis as needed. Following placement of the interbody implant, the remainder of the posterior spinal fixation procedure including placing spinal rods may completed per specific technique.

It should be understood, of course, that the foregoing relates to exemplary embodiments of the invention and that modifications may be made without departing from the spirit and scope of the invention as set forth in the following claims.

We claim:

1. A spinal procedure, comprising:
   attaching a first reduction instrument to a first guide assembly and a second guide assembly with the patient in the lateral decubitus position, wherein the first reduction instrument comprises a handle, a body, and a translating attachment assembly;
   attaching the first guide assembly to a first pedicle;
   attaching the second guide assembly to a second pedicle; and
   with the patient positioned in the lateral decubitus position, moving the first reduction instrument handle downward toward the spine causing the body to pivot around the translating assembly to reduce an orientation of the spine.

2. The procedure of claim 1, wherein the reduction of the spine includes reducing a spondylolisthesis of the spine.

3. The procedure of claim 1, further comprising inserting a plurality of pedicle screws into the spine prior to reduction of the orientation of the spine.

4. The procedure of claim 3, further comprising using an oblique fluoroscopic view of the first and second pedicles while inserting the pedicle screws.

5. The procedure of claim 3, further comprising using a bilateral fluoroscopic view of the first and second pedicles while inserting the pedicle screws.

6. The procedure of claim 1, further comprising imaging a reduction of the orientation of the spine.

7. The procedure of claim 1, further comprising using a second reduction instrument relative to one of the first guide assembly and the second guide assembly.

8. The procedure of claim 7, wherein the first and second reduction instruments are different types of instruments.

9. The procedure of claim 7, wherein the first and second reduction instruments are the same types of instruments.

10. A spinal procedure, comprising:
    attaching a first reduction instrument to a pair of first guide assemblies while a patient is in a lateral decubitus position, wherein the first reduction instrument comprises a handle, a body, and a first translating attachment assembly;
    attaching a second reduction instrument to a pair of second guide assemblies while the patient is in the lateral decubitus position;
    attaching the first guide assemblies to upside pedicles;
    attaching the second guide assemblies to downside pedicles;
    with the patient positioned in the lateral decubitus position, moving the first reduction instrument handle downward toward the spine causing the body to pivot around the first translating assembly to reduce an orientation of the spine; and
    locking an angle and position of the first reduction instrument upon achieving a desired reduction.

11. The procedure of claim 10, wherein the first reduction instrument includes a first fixed attachment assembly and a first translating attachment assembly that cooperatively interfaces the first fixed attachment assembly.

12. The procedure of claim 10, wherein the second reduction instrument includes a second fixed attachment assembly and a second translating attachment assembly that cooperatively interfaces the second fixed attachment assembly.

13. The procedure of claim 10, wherein the pair of the first guide assemblies are superior and inferior guide assemblies.

14. The procedure of claim 10, wherein the first guide assemblies are attached to the upside pedicles before the second guide assemblies are attached to the downside pedicles.

15. The procedure of claim 10, wherein the reduction of the orientation of the spine includes reducing a spondylolisthesis of the spine.

* * * * *